(12) United States Patent
Suckau et al.

(10) Patent No.: US 7,396,686 B2
(45) Date of Patent: Jul. 8, 2008

(54) BIOPOLYMER SEQUENCES BY MALDI GRANDDAUGHTER ION SPECTRA

(75) Inventors: Detlev Suckau, Grasberg (DE); Anja Resemann, Ganderkesee (DE)

(73) Assignee: Bruker Daltonik GmbH, Bremen (DE)

( * ) Notice: Subject to any disclaimer, the term of this patent is extended or adjusted under 35 U.S.C. 154(b) by 929 days.

(21) Appl. No.: 10/758,958

(22) Filed: Jan. 16, 2004

(65) Prior Publication Data

US 2004/0197826 A1    Oct. 7, 2004

(30) Foreign Application Priority Data

Jan. 17, 2003    (DE) ............... 103 01 522

(51) Int. Cl.
*G01N 24/00* (2006.01)
(52) U.S. Cl. .................... 436/173
(58) Field of Classification Search .......... None
See application file for complete search history.

(56) References Cited

U.S. PATENT DOCUMENTS 5,734,161 A    3/1998   Köster
6,300,627 B1   10/2001  Köster et al.

FOREIGN PATENT DOCUMENTS

GB    2 260632 A     10/1992
WO    WO 98/03684 A1  1/1998

OTHER PUBLICATIONS

Brown et al. "Sequence-specific fragmentation of matrix-assisted laser-desorbed protein/peptide ions" Anal. Chem., 1995, v. 67, pp. 3990-3999.*
Takayama et al. "Does in-source decay occur independent of the ionization process in matrix-assisted laser desorption?", INt. J. Mass Spectrim., 1998, v. 181, L1-L6.*
Suckau et al. "T3-sequencing: targeted characterization of the N- and C-termini of undigested proteins by mass spectrometry", ANal. Chem., 2003, v. 75, pp. 5817-5824.*
Suckau et al. "A novel MALDI Lift-TOF/TOF mass spectrometer for proteomics", Anal. Bioanal. Chem., 2003, v. 376, pp. 952-965.*
Liu et al. "Optimization of a MALDI TOF-TOF mass spectrometer for intact protein analysis", J. Am. Soc. Mass Spectrom., 2005, v. 16, pp. 482-490.*

(Continued)

*Primary Examiner*—Yelena G Gakh
(74) *Attorney, Agent, or Firm*—Law Offices of Paul E. Kudirka

(57) ABSTRACT

The invention relates to the acquisition of spectra of biopolymers, especially of proteins, in tandem mass spectrometers with ionization using matrix-assisted laser desorption (MALDI) for the examination or determination of sequence patterns. The invention consists of a method of measuring granddaughter spectra of terminal fragment ions of the bipolymers in tandem mass spectrometers, wherein a so-called in-source fragmentation to generate a first generation of fragment or daughter ions of a biopolymer is coupled with a subsequent measurement of granddaughter ions, which have been obtained by a further fragmentation of a selected type of daughter ions. The method according to the invention enables the determination of the terminal sequences which are otherwise very difficult to measure.

14 Claims, 3 Drawing Sheets

OTHER PUBLICATIONS

Köcher et al. "Fragmentation of peptides in MALDI in-source decay mediated by hydrogen radicals", Anal. Chem., 2005, v. 77, pp. 172-177.*

Wuhrer et al. "Matrix-assisted laser desorption/ionization in-source decay combined with tandem time-of-flight mass spectrometry of permethylated oligiosaccharides: targeted characterization of specific parts of the glycan structure", Rapid Commun. Mass Spectrom., 2006, v,. 20, pp. 943-951.*

Toyoda et al. High-energy collison induces dissociation fragmentation pathways of peptides, probed using multiturn tandem time-of-flight mass spectrometer "Multi-TOF/TOF", Review of Scientific Instruments, 2007, v. 78, 074101-1-074101-9.*

Johnson, Richard S., et al., "Collision-Induced Fragmentation of $(M+H)^+$ Ions Of Peptides. Side Chain Specific Sequence Ions", International Journal of Mass Spectrometry and Ion Processes, vol. 86, Elsevier Science Publishers B.V., 1988, pp. 137-154.

Reiber, Duane C., et al., "Unknown Peptide Sequencing Using Matrix-Assisted Laser Desorption/Ionization and In-Source Decay", Analytical Chemistry, vol. 70, No. 6, American Chemical Society, Mar. 15, 1998, pp. 1214-1222.

Search Report.

* cited by examiner

BIOPOLYMER SEQUENCES BY MALDI GRANDDAUGHTER ION SPECTRA

FIELD OF THE INVENTION

The invention relates to the acquisition of spectra of biopolymers, especially of proteins, in tandem mass spectrometers with ionization using matrix-assisted laser desorption (MALDI) for the examination or determination of sequence patterns.

BACKGROUND OF THE INVENTION

The mass spectrometric determination of the terminal sequence patterns of larger proteins, including possible modifications to these sequences, is usually difficult. Even non-mass spectrometric methods, for example Edman sequencing, which usually makes it possible to at least determine the N-terminal sequence, fail in the case of N-terminal modifications.

In mass spectrometers with MALDI ion sources it is not possible to achieve a uniform fragmentation of larger proteins right up to the termini. While it is possible to directly ionize larger proteins with simultaneous fragmentation with a so-called in-source decay (ISD), it is not possible to identify the terminal sequence patterns because of extremely noisy spectra in the lower mass range.

The use of electrospray ionization, suitable for large molecules, is usually coupled with the use of ion trap mass spectrometers or quadrupole filter mass spectrometers. Although in such cases the ions of the proteins can be fragmented (with difficulty), the small ions of the terminal fragments cannot be measured because of the lack of storage capability of these spectrometers in the lower mass-to-charge range.

With a preceding enzymic digest of the larger proteins, as used for the identification of proteins by means of 'fingerprint spectra', the terminal digest peptides can, in principal, no longer be identified as such. One solution is the biochemical labeling of the N or C termini in such a way that they can be identified as terminal in the mass spectra. This method also fails, however, when the enzymic splitting occurs relatively close to one of the termini; the digest peptide which is produced is then too short to be detected using mass spectrometric methods; different types of mass spectrometers have very different reasons why this is the case.

The determination of the terminal sequences is, however, important in various areas of application. One example is the examination of the terminal sequences for the quality control of synthesized proteins. The frequently used method of recombinant syntheses using introduced genes in production bacteria (usually for *E. coli*) experiences problems with the clean splitting off of the detector sequences (for example His tags) or with the detection of the stop codons by the bacteria's own polymerases. Chemical synthesis also experiences problems with undesired modifications to the protein ends.

To investigate sequences of biopolymers, tandem mass spectrometers are usually employed. These originally consisted of two spatially separated mass spectrometers with a collision cell to fragment the ions placed between them. In the first spectrometer, ions of a particular type were selected, and these were then at least partially fragmented in the collision cell. The 'fragment ions' or 'daughter ions' thus generated were then analyzed in the second spectrometer; the result is a 'daughter ion spectrum'. One example is the 'triple quad mass spectrometer', which has an additional quadrupole as a collision cell between two quadrupole filter mass spectrometers. In addition to this principal of 'tandem in space', the principal of 'tandem in time' has recently appeared: In a storage mass spectrometer, ion selection, fragmentation and the scanning of the daughter ion spectra are carried out consecutively in the same storage cell. High frequency ion trap mass spectrometers or Fourier transform mass spectrometers (FTMS) are used as the storage mass spectrometers. The measuring methods for scanning the daughter ion spectra are often known as MS/MS methods for short.

Tandem time-of-flight mass spectrometers, among others, are used to acquire daughter ion spectra with ionization by means of matrix-assisted laser desorption (MALDI). They consist of a first spectrometer with an ion selector to select the ions which are to be investigated and the daughter ions formed from them, and a second spectrometer for analyzing the daughter ions. Tandem time-of-flight mass spectrometers for this measurement method with ionization by matrix-assisted laser desorption (MALDI) are available commercially and are often known as TOF/TOF mass spectrometers. Ionization using MALDI is favorable in that, in the main, only singly charged molecular ions of the analyte substances are formed. This makes it possible to mix different substances in one sample, for example the different tryptic digest peptides of a protein, and to then investigate the ions of these substances one after the other to look at the daughter ions they produce.

For ease of expression, the ions of the ion type primarily formed, whose structure is to be examined using fragmentation, are termed 'selection ions'. This nomenclature is chosen because the ions of this type have to be selected from the mixture of primary ions in some way, regardless of whether this selection occurs before or after subsequent fragmentation. This selection usually occurs with the first mass spectrometer of a tandem mass spectrometer. Out of these selection ions, different decay processes now create 'fragment ions of a first fragmentation generation' and neutral fragments which are invisible to a mass spectrometer. These fragment ions of the first fragmentation generation are here termed simply 'fragment ions' or 'daughter ions'. After a decay, the selection ion ceases to exist, of course. Usually, however, there are always sufficient selection ions remaining in an undecayed state so that their signal can also be seen in the daughter ion spectrum.

The daughter ions can be broken down further by different processes to form 'fragment ions of the second generation', generally termed 'granddaughter' ions here. In the granddaughter ion spectrum, daughter ions can usually still be seen since even the second fragmentation does not usually affect all the daughter ions.

As is widely known, two different fragmentation methods are available in TOF/TOF devices for the fragmentation of the selection ions into daughter ions: collisional fragmentation in a collision gas in a collision cell (CID=Collisionally Induced Decomposition) and metastable decay of ions as a result of increased energy absorption in the laser generated plasma within the MALDI ion source (LID=Laser Induced Decomposition). Both types of decay occur after the ions, including the selection ions, have been accelerated in the field-free flight path of the first time-of-flight mass spectrometer. In both cases, the daughter ions of the selection ions generated in each case therefore fly at the same velocity as the selection ions which have not decayed. After a velocity dispersive flight path, it is therefore possible to use an ion selector to time select the daughter ions, together with the non-decayed selection ions, from all the ions generated in the ion source, for subsequent analysis in the second spectrometer. The precise procedure for this selection and the subsequent analysis of the daughter ions after an intermediate acceleration before the second time-of-flight mass spectrometer will not be discussed further here. The basic principle of a TOF/TOF mass spectrometer is described in the patent U.S. Pat. No. 6,300,627 (corresponding to DE 198 56 014 C1).

The non-spontaneous metastable decay (LID) of the ions is preceded by an internal thermalization, i.e. a statistical equipartitioning of the excess energy absorbed in the laser plasma over all the oscillation systems of the ion. The bonds in the chain-like ion resemble a complicated system of coupled oscillations in which the available energy is continuously statistically redistributed by the coupled oscillation processes. If, at a relatively weak bonding point in the chain of the molecule, the momentarily accumulated energy exceeds the bonding energy at this point, the chain may be broken at this point. This creates primarily daughter ions of the b and y fragmentation series; in addition there are frequently also ions of the (b-17) series.

The nomenclature used here is based on that of Roepsdorf and Fohlmann as revised by Johnson, Martin, and Biemann in 1988 (Int. J. Mass Spectrom. Ion Proc. 86, 137-154). The basic fragmentation series a, b, c, x, y and z and their indices are shown schematically in FIG. 1. If a singly charged protein ion is divided at the bonding point between the amino group of the preceding amino acid and the carboxyl group of the subsequent amino acid, we refer to fragment ions of the b series when it involves N-terminal ions, and of ions of the y series when it involves C-terminal ions. To distinguish between the fragmentation series b and y it is important to know on which of the two resulting fragments the ionizing proton remains. In each case, the other end becomes the neutral fragment. (In the case of fragmentation of doubly charged protein ions, both N- and C-terminal fragment ions can be formed; this is scarcely possible in the case of the singly charged MALDI ions which form the vast majority). Indices on the letters b or y indicate which fragmentation point in the ion has been split; for b ions, the count begins at the N-terminus, for y ions at the C-terminus.—If the splitting takes place one carbon atom further towards the N-terminal end, we speak of ions of the a or x series, with an analog count for the indices. If it takes place further towards the C-terminal (at the other side of the nitrogen atom), we obtain ions of the c or z series. In addition there are frequently still ions where, for example, $NH_3$, and occasionally also $H_2O$, is split off; they are then termed ions of the (b-17) series (or the (b-18) series) with indices which are appended to the parentheses. (Sometimes, the parentheses are also omitted in spectra in the interests of a short representation).

Since, in each case, the weakest bonds (those bonds which lead to b or y series) between the amino acids of a peptide do not all possess the same bonding energy but instead have very different energies, certain bonds are broken less frequently than others. As an example, the bonds of proline to proline are stronger than the average bond between amino acids; these bonds are therefore by far less frequently fragmented and the resulting fragment ions occur less frequently. The corresponding mass signals in the spectrum (peaks) are therefore much weaker (if at all visible) than those of other fragment ions.

Collisionally induced decay (CID) is distinguished from metastable decay by the fact that ions additionally appear which are generated by side chain fragmentations (so-called d or w ions). Ions can also suffer double fragmentations, so that non-terminal ('internal') fragment ions can arise, which are then termed $b_n y_m$.

The daughter ion spectra of digest peptides generated in TOF/TOF mass spectrometers are generally used for the confirmation of protein identifications which have been initially obtained from so-called 'fingerprint spectra' of the enzymic digest peptides of the protein. The confirmation of these identifications by means of the daughter ion spectra of individual digest peptides is carried out with the help of so-called search programs which work in databases with hundreds of thousands of stored protein sequences. Various search programs of this type are commercially available.

Furthermore, the daughter ion spectra are used for the de-novo sequence determination of proteins whose sequences are not contained in the database. However, these sequence determinations, for which commercial computer programs are also available, are difficult and usually not unequivocal, so that one usually receives a number of suggestions. The daughter ion spectra with their mix of b, y, internal and (b-17) ions are very complex, hence the sequence determination is often not unequivocal and frequently also only successful for partial sequences. For this reason, methods are urgently required which permit a simpler and clearer cut de-novo sequence determination.

A third type of ion fragmentation in MALDI mass spectrometers has been known for a long time, although until now it has rarely been used and for reasons not yet established it has not functioned with the same level of success in all commercial MALDI ion sources: in-source decay (ISD), which is generated simply by a higher laser energy density in the MALDI process (see, for example, D. C.Reiber et.al., "Unknown Peptide Sequencing Using Matrix-Assisted Laser Desorption/Ionization and In-Source Decay", Anal. Chem. 1998, 70, 1214-1222). A fundamental difference between this method of daughter ion generation and the other two fragmentation methods is that, in this case, the fragmentation occurs spontaneously (within $10^{-8}$ seconds at the most) before the acceleration of the ions in the ion source. The delayed acceleration of the ions (DE=delayed extraction) nowadays used without exception for MALDI ion sources produces a clear separation of the decay period and the acceleration phase; the spontaneously decaying ions can thus be cleanly detected since these spontaneous decay processes are more or less complete when, after a few $10^{-8}$ seconds, the acceleration sets in. After leaving the ion source, the fragment ions thus have different velocities depending on their mass. These types of fragment ions can therefore be separated and analyzed in a simple time-of-flight mass spectrometer. This fragmentation functions particularly well for intact proteins in a molecular weight range of 2000 to about 70,000 atomic mass units.

For the application of in-source fragmentation it is, however, necessary that the analyte substances of the ion source are introduced separately and are moderately pure, since otherwise the spectra which are produced are so complex that it is no longer possible to interpret them. For this method, therefore, when the sample is prepared on a sample support, only one single analyte substance mixed with the matrix substance is applied. The application of a digest mixture is no longer required; the great advantage of this ionization and fragmentation is precisely that it can be used for large peptides up to large proteins.

In-source fragmentation is not an MS/MS method in the real sense because the first mass spectrometer, which selects the ions to be investigated from the complex ion mix, is missing. This selection of the 'selection ions' is instead performed (before any ionzation) by an external cleaning process for the investigated substance, for example chromatographic cleaning. The use of a synthesized substance, for example a recombinant protein, is also possible at this point. The application of a single pure substance is particularly necessary for more complex substances, such as proteins. If several proteins, whose ions decay into a very large number of daughter ions, were applied in comparable concentrations, the resulting spectra would be so complex that it would no longer be possible to decode them. This method is therefore only suitable for determining the structure of relatively pure substances.

Even though one cannot speak of an MS/MS method, it is without doubt the case that, as in an MS/MS method, fragment or daughter ions of the substance under investigation are measured. The method is sometimes called a 'pseudo-MS/MS' method.

The daughter ion spectra obtained by in-source decay (ISD) are very different in appearance to the daughter ion spectra obtained by CID or LID. The type of fragmentation of the in-source decay is, in all probability, a so-called electron capture dissociation (ECD), and it is indeed possible to observe that the fragment ion spectra of the ISD, with their strong preference for the c fragment ion series, have a high degree of similarity to the daughter ion spectra obtained in suitable mass spectrometers by means of ECD.

The spontaneous fragmentations which occur in the explosion plasma of the laser bombardment when the laser energy density is slightly increased probably occur in those ions which were initially doubly charged in the hot laser plasma as a result of double protonation, as is the case with ECD. If these ions are neutralized by one charge state by the electrons present at the same time, then the ionization energy (more accurately: the proton affinity energy) is released and transformed into oscillation energy. The energy transferred to the ion at a single point is so high that it immediately (in less than $10^{-8}$ seconds) causes the chain-shaped molecule in the immediate vicinity of the recombination point to break. One of the halves of the molecule carries the remaining charge and is thus an ion which can be analyzed, while the other half becomes a neutral particle which eludes further mass spectrometric analysis.

Protein spectra which arise through ISD primarily contain daughter ions of the c series for N-terminal ions, which are present in noticeably high ion signals, and the y series for C-terminal ions. As a result of the ring structure of proline, however, the C ions from the fragmentations in front of the prolines are completely absent because they would have to break open a double bond. The c ions do not end in COH at the C-terminus—as the b ions do—but instead they end in an amide structure ($CONH_2$). For smaller ions, a ions also occur. The fragmentation is strongly matrix and size dependent, however. When α-cyano-4-hydroxy-cinnamic acid (CHCA) is used as matrix, there are significantly more daughter ions of the a series; their intensity is much lower when 2,5-dihydroxy-benzoic acid (DHB) is used, and when 3,5-dimethoxy-4-hydroxy-sinapic acid (sinapic acid) is used as matrix, only very few are found.

As a result of the localization probability of the neutralized proton, which is distributed roughly equally over the length of the protein, all the bonds between the amino acids are equally affected by the fragmentations, one exception being the fragmentations toward the prolines. All fragment ions of different lengths are therefore formed in roughly the same concentrations; this is completely different to the situation with CID and LID. Here, as well, a similarity to ECD spectra can be seen.

In-source fragmentation, however, has one disadvantage which cannot be ignored: The spectra in the range of the light ions up to a mass of 1000 atomic mass units, approximately, which are important for the analysis of protein ends, for example, are very strongly contaminated and noisy because of numerous fragments of the matrix substance and their oligomers and also, possibly, because of other small ions which have arisen as a result of reactions of many different types in the hot MALDI plasma. A meaningful interpretation of the spectra is only possible above around 1000 mass units; to avoid overloading the ion detector with an excess of small ions, ISD spectra are only ever recorded above a mass unit of 1000. For proteins, this means that the sequence of the first eight amino acids is unidentifiable. It is precisely this terminal sequence, which is of such interest for many analytical purposes, which evades analysis.

It is, however, advantageous that the spectra of the ISD fragment ions extend uniformly up to the higher mass ranges at around 5000 mass units, when larger proteins are measured. There is one exception, when the protein has a cross link, for example a disulfide bridging bond between two cysteines. At the cross link, the respective b or y ISD fragment ion series abruptly breaks off because here, two bonds each would have to be broken.

The fragment ions created by in-source decay are highly excited and therefore strongly metastable again in themselves, and decay to a large extent on the flight through the mass spectrometer. In line with current thinking, they are therefore measured only in linear mass spectrometers (without reflector or without using the reflector) since, in this case, the fragment ions and the granddaughter ions arising from some of these as a result of decay arrive at the same time and provide strong signals, even though the mass resolving power is not satisfactory for a good mass determination. Since the decays also always convert any bonding energy which is released into kinetic energy, i.e. some ions accelerate and others decelerate, the ion signal broadens and thus worsens the mass resolving power. According to current opinion, a measurement in a reflector time-of-flight would lead to spectra which are even noisier than those measured in linear spectrometers.

Contrary to current teaching, the use of a reflector, on the other hand, leads to good spectra with a much improved mass resolution, whereby the noise in the mass range between 1000 and 5000 atomic mass units, which is actually quite strong in the linear mode, is not noticeable. In this mass range, good resolutions of the isotope structure are consistently achieved, with a corresponding accuracy of the mass determination.

Its uniform fragmentation and good mass accuracy for the fragments would thus make this fragmentation method eminently suitable for determining sequences of larger proteins. It fails, however, because it is precisely the terminal sequences of proteins which cannot be detected because of the noisy spectrum. The objective of the invention, therefore, is the generation of biopolymer spectra which contain information about the terminal sequences of the building blocks of biopolymers.

SUMMARY OF THE INVENTION

The invention involves a method of measuring granddaughter spectra of terminal fragment ions of the bipolymers in tandem mass spectrometers, wherein a so-called in-source fragmentation to generate a first generation of fragment or daughter ions of a biopolymer is coupled with a subsequent measurement of granddaughter ions, which have been obtained by a further fragmentation of a selected type of daughter ions. This enables the determination of the terminal sequences which are otherwise very difficult to measure. The tandem mass spectrometer (with an ion source to ionize the biopolymer by means of matrix-assisted laser desorption) initially generates ISD fragment ions of the biopolymers using high laser energy density in the ion source. One type of these ISD fragment ions is then subjected to a further fragmentation by means of gas collisions (CID=collision induced decomposition), surface collisions (SID=surface induced decomposition), photon collisions (PID=photon induced decomposition) or metastable decay (LID=laser induced decomposition). The granddaughter ions are thus created as a mass spectrum. The granddaughter spectra reach down to the C- and N-termini and reveal the terminal sequences.

In the following, the method of producing the granddaughter ions is indicated by prefixing the abbreviations of the fragmentation mechanisms: ISD-LID granddaughter ions are thus ions which have been created by metastable decay (LID=laser induced decomposition) from ISD fragment ions (ISD=in-source decay).

Broken down into individual method stages, the invention involves preparing one distinct biopolymer mixed with matrix substance on a sample support, introducing the sample support into the ion source, subjecting the prepared sample to fragment ion generation with in-source decay in a tandem mass spectrometer by means of laser bombardment with an energy density greater than that normally used in MALDI, selecting—in the first spectrometer—ions of a single type thus generated and further fragmenting them using the fragmentation mechanism of the respective tandem mass spectrometer, and, finally, acquiring a granddaughter ion spectrum by a mass dispersive measurement of the granddaughter ions thus created in the second mass spectrometer. In particular, a tandem time-of-flight mass spectrometer (TOF/TOF-MS) can be used for this.

A particularly favorable method of determining the terminal sequences of a biopolymer involves initially scanning at least two granddaughter ion spectra according to the invention, said spectra being acquired of different species of ISD fragment ions of the same fragmentation series (e.g. the c series). By comparing these granddaughter ion spectra from different ISD fragment ions, the N-terminal and C-terminal ion series (i.e. for LID fragmentations normally the b and y series) can be determined because, in each case, one ion series is fixed in the two or more granddaughter spectra, and the ion series running in the opposite direction shifts from spectrum to spectrum. From the fix ion series of two c series granddaughter ion spectra, which now only contain the b ions, the mass differences can be used to read off the N-terminal sequence pattern of the building blocks of the biopolymer. In a similar manner, from the fix ion series of two y series granddaughter ion spectra, the mass differences can be used to read off the C-terminal sequence pattern. This type of determination of the terminal sequences can easily be undertaken using a suitable computer program.

BRIEF DESCRIPTION OF THE DRAWINGS

The above and further advantages of the invention may be better understood by referring to the following description in conjunction with the accompanying drawings in which.

DETAILED DESCRIPTION

In mass spectrometers, it is actually only the mass-to-charge ratios (m/z) of the ions that are measured, and never the masses of the ions themselves. The spectra are never "mass spectra" but more "mass-to-charge-spectra". However, since, in the MALDI process, practically only singly charged ions are generated, the value for the charge is practically always a unit charge (z=1), therefore in the interest of simplicity one can speak here simply of the mass of the ions. When, in the following, the terms "light ions" or "lower mass range of the spectrum" are used, they are to be understood in this context.

The invention consists in initially subjecting the pure biopolymer samples mixed with matrix substance on a sample support to an in-source fragmentation of the protein ions generated in the MALDI process by increasing the laser energy density, this taking place in a normal tandem mass spectrometer, which operates with an ionization by means of matrix-assisted laser desorption; then injecting the ISD fragment ions thus generated into the first mass spectrometer, selecting a suitable ion species here and using the first mass spectrometer to fragment this ion species, and mass dispersively measuring the granddaughter ions thus generated as a granddaughter ion spectrum in the second mass spectrometer. The terminal sequence patterns of the biopolymers, in particular, can be determined from these granddaughter ion spectra.

Here, the term biopolymers is taken to mean proteins and their conjugates, such as glycoproteins or lipoproteins, in general and also genetic material or polysaccharides.

In the following, the description of the method of gathering information about sequence patterns is limited, as an example, to protein molecules and the use of a tandem time-of-flight mass spectrometer with a second fragmentation by metastable decay of the ISD fragment ions, but the invention should not be restricted by these limitations. The following therefore assumes an unmodified commercial TOF/TOF mass spectrometer even though a method according to the invention can also be realized on other types of tandem mass spectrometer.

Figure 1:
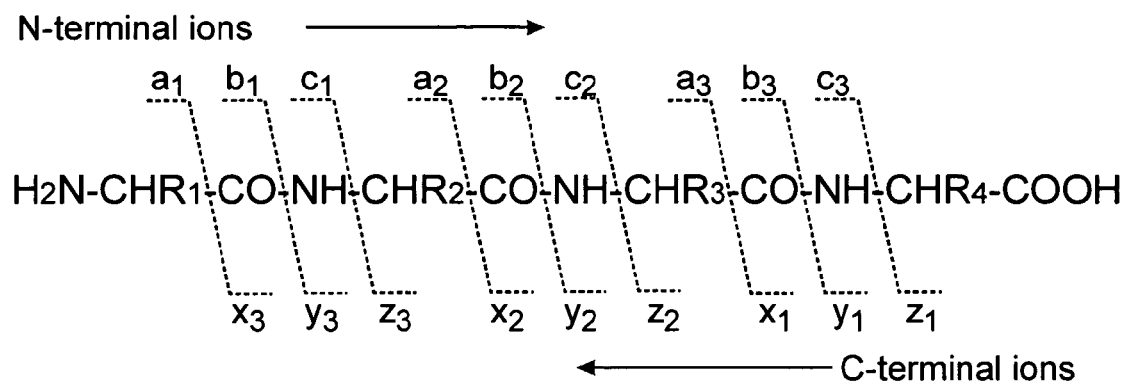
FIG. 1 describes the nomenclature of the fragment ion series for proteins by means of a schematic example.
Figure 2:
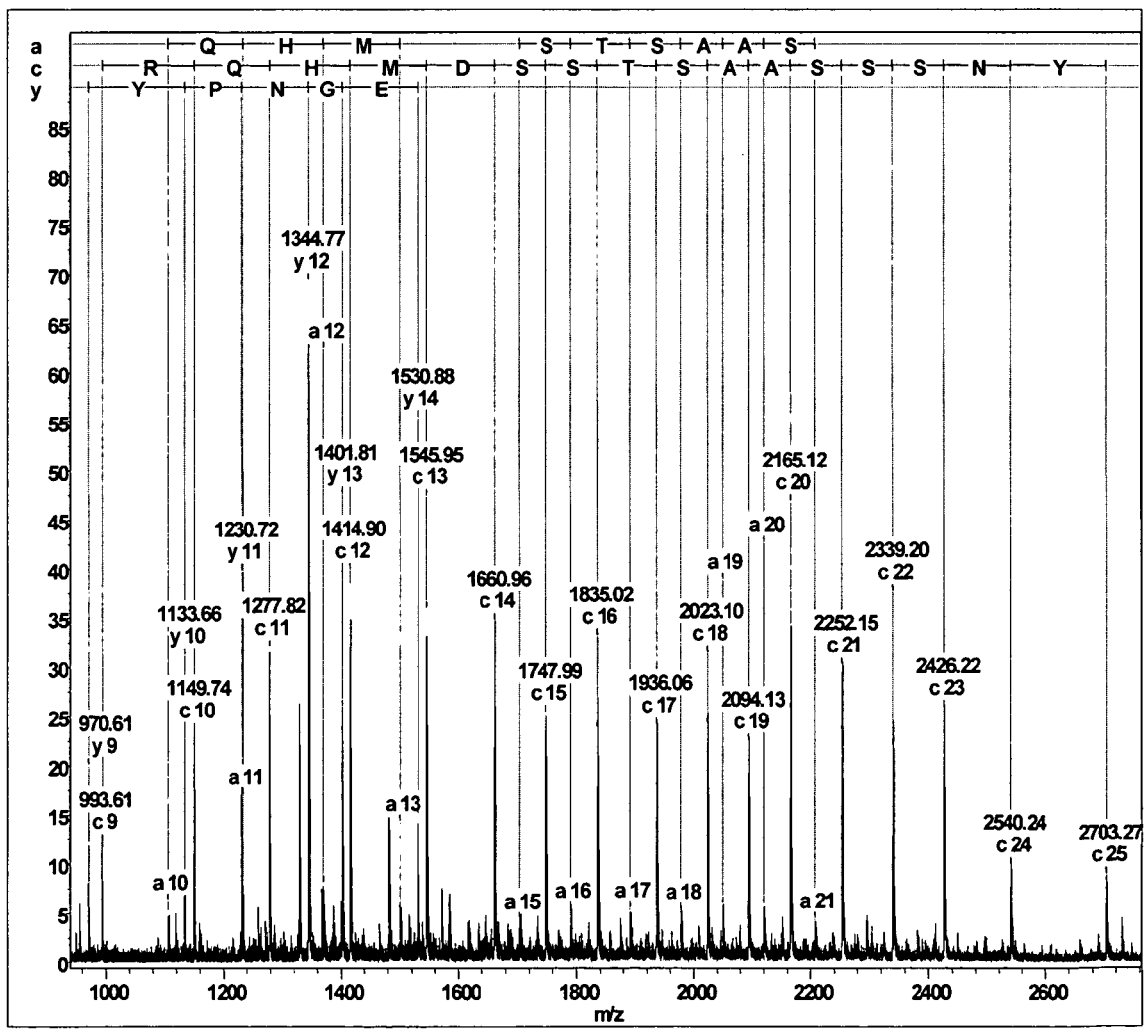
FIG. 2 presents the ISD spectrum of the RNase-B enzyme in the mass range from 1000 to 2800 atomic mass units with a clearly defined c fragment ion series from $c_9$ to $c_{25}$. The y fragment ion series breaks off at $y_{12}$ because, at this point, there is a cross link of a cysteine. The spectrum was recorded using DHB as the matrix substance.
Figure 3:
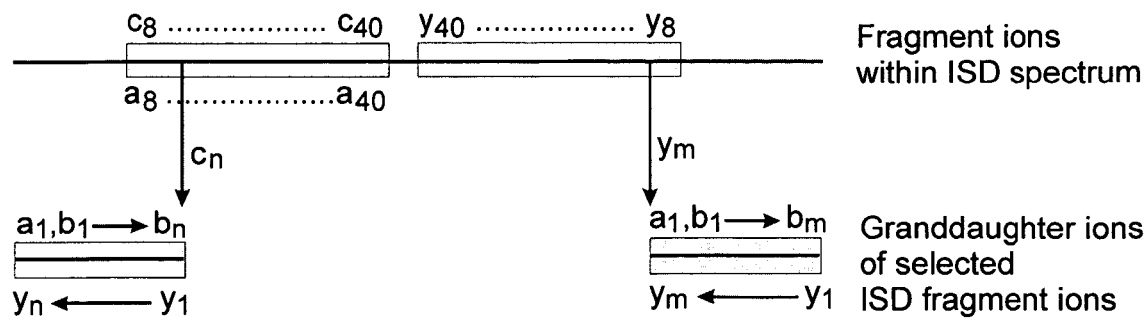
FIG. 3 illustrates the schematics and contents of the ISD-LID granddaughter ion spectra, in each case originating from a c ISD fragment ion and a y ISD fragment ion.

A spectrum of the ISD fragment ions is initially measured in the normal reflector mode of the tandem time-of-flight mass spectrometer, i.e., with TOF/TOF mode switched off. An ISD fragment ion spectrum of this type is shown in FIG. 2. In this case, only the mass range above 1000 atomic mass units is detected in order to avoid overloading the detector with the high number of noisy light ions below 1000 mass units. The spectrum thus generated serves as a base for the selection of the ISD fragment ions for the granddaughter ion spectrum acquisition.

To select the ISD fragment ions for further investigation it is favorable if the ISD spectrum can already be interpreted to the degree that the ion signals of the c, a or y series can be assigned.

The interpretation can be simplified by the choice of matrix substance. Protein spectra which are generated by ISD generally contain primarily daughter ions of the c series for N-terminal ions. When α-cyano-4-hydroxy-cinnamic acid (CHCA) is used as the matrix, the intensity of the daughter ions of the a series is now similar to that of the c ions. Since the mass difference is 45 mass units, the a/c ion pairs are easy to find. For reasons which are well-known, the use of CHCA also leads to the most accurate mass determinations. The explanation of these reasons is beyond the scope of this work. Conversely, CHCA is extremely disadvantageous for the generation of ISD-LID granddaughter ion spectra because the ISD fragment ions, which are highly excited with CHCA, decay into many small pieces of debris.

The use of 2,5-dihydoxy-benzoic acid (DHB) leads to much lower intensities of the a ions (FIG. 2), with acceptable intensities for the y ions. The mass accuracy of the ISD fragment ion spectra is only moderately good. However, DHB produces the best ISD-LID granddaughter ion spectra.

If 3,5-dimethoxy-4-hydroxy-sinapic acid ('sinapic acid') is used as the matrix, the c ions are very evident as a series while the y ions diminish in importance and the a ions are practically invisible. Sinapic acid is therefore particularly suitable for recognizing the series of the c ions. The generation of ISD-LID granddaughter ion spectra with sinapic acid, on the other hand, is difficult; it is, however, possible that these sinapic acid ISD fragment ions are eminently suitable for further fragmentation by collisions (CID).

For the measurement of the metastably generated ISD-LID granddaughter ions of the selected ISD fragment ions which arise, the mass spectrometer is switched to TOF/TOF operation. Further laser bombardment then enables any ISD fragment ion to be selected from the ion mixture, and the ISD-LID granddaughter ion spectra generated by metastable decay from these ions can be measured.

Figure 4:
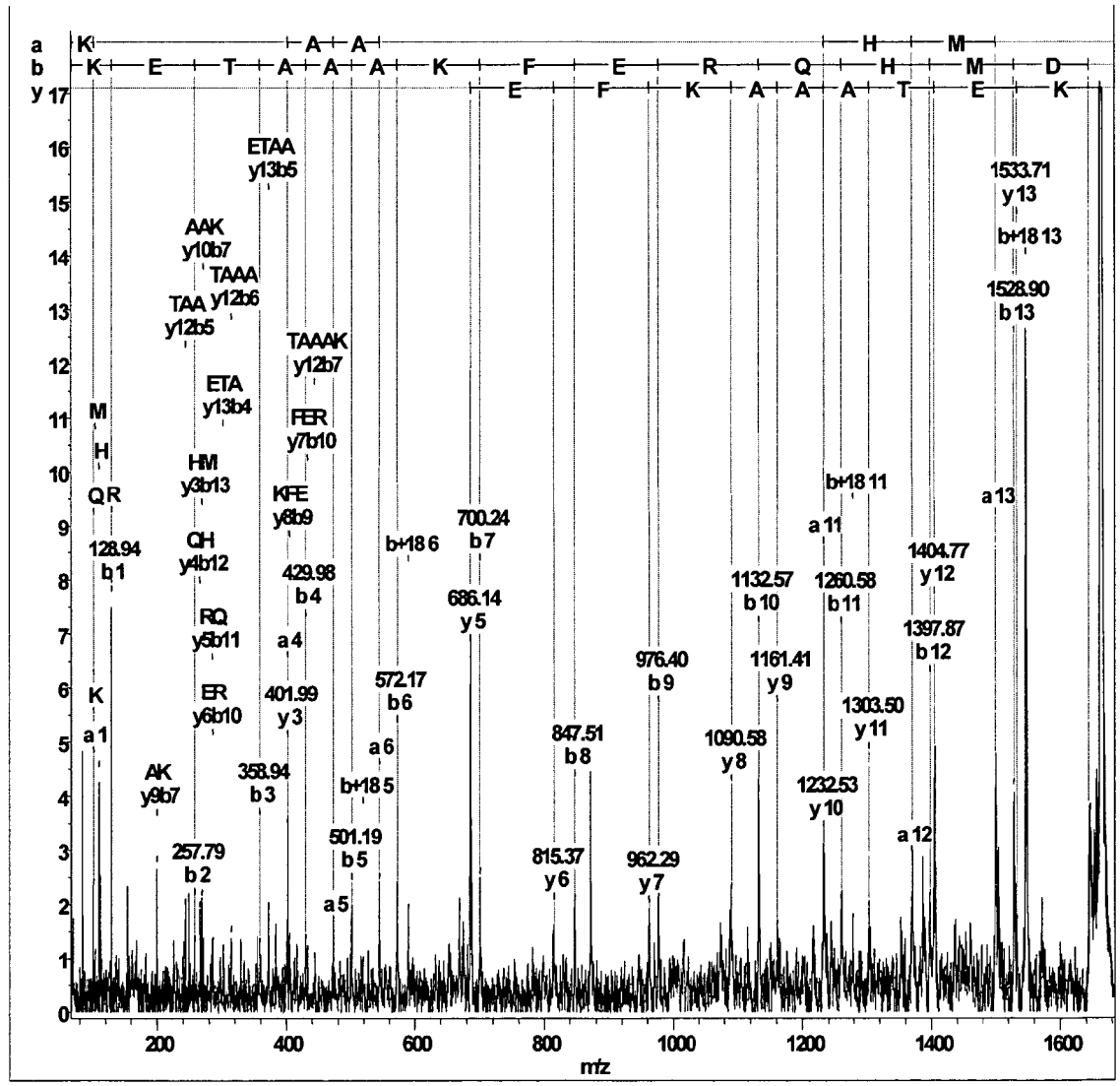
FIGS. 4 and 5 show the ISD-LID granddaughter ion spectra, respectively, of the $C_{14}$ ISD fragment ion and the $y_{12}$ ISD fragment ion of the RNase-B, both generated by a DHB matrix.

If the selected ISD fragment ions belong to the a or c series (FIG. 4 shows the ISD-LID granddaughter ion spectrum of a $C_{14}$ ISD fragment ion) then metastable decay produces ISD-LID granddaughter ion spectra which consist primarily only of ion signals of the b and the y series, with an admixture of some ions of the a series. Peptide amide ions are produced from ions of the c series; the indices of the y series in FIG. 4 are now directed towards these peptide amide ions (no longer to the original protein). In the noise-free granddaughter ion spectrum, the ion signals of the b and y series extend up to the terminal amino acid and confirm the sequence from the N-terminus up to the mass of the selected fragment ions, if known. In FIG. 4, the amino acids of the known sequence of the RNase-B, which are identifiable from the mass differences, are shown above the spectrum; this confirms the correct sequence of the N-terminus. Since the inner energy of the ISD fragment ions is very high, double fragmentations also create several so-called immonium ions, which are created from individual amino acids and indicate the presence of these amino acids in the ISD fragment ion. There are also a number of internal ISD-LID granddaughter ions present which consist of between two and five internal amino acids. If these internal ions are very prevalent, they make it more difficult to interpret the granddaughter ion spectrum.

Figure 5:
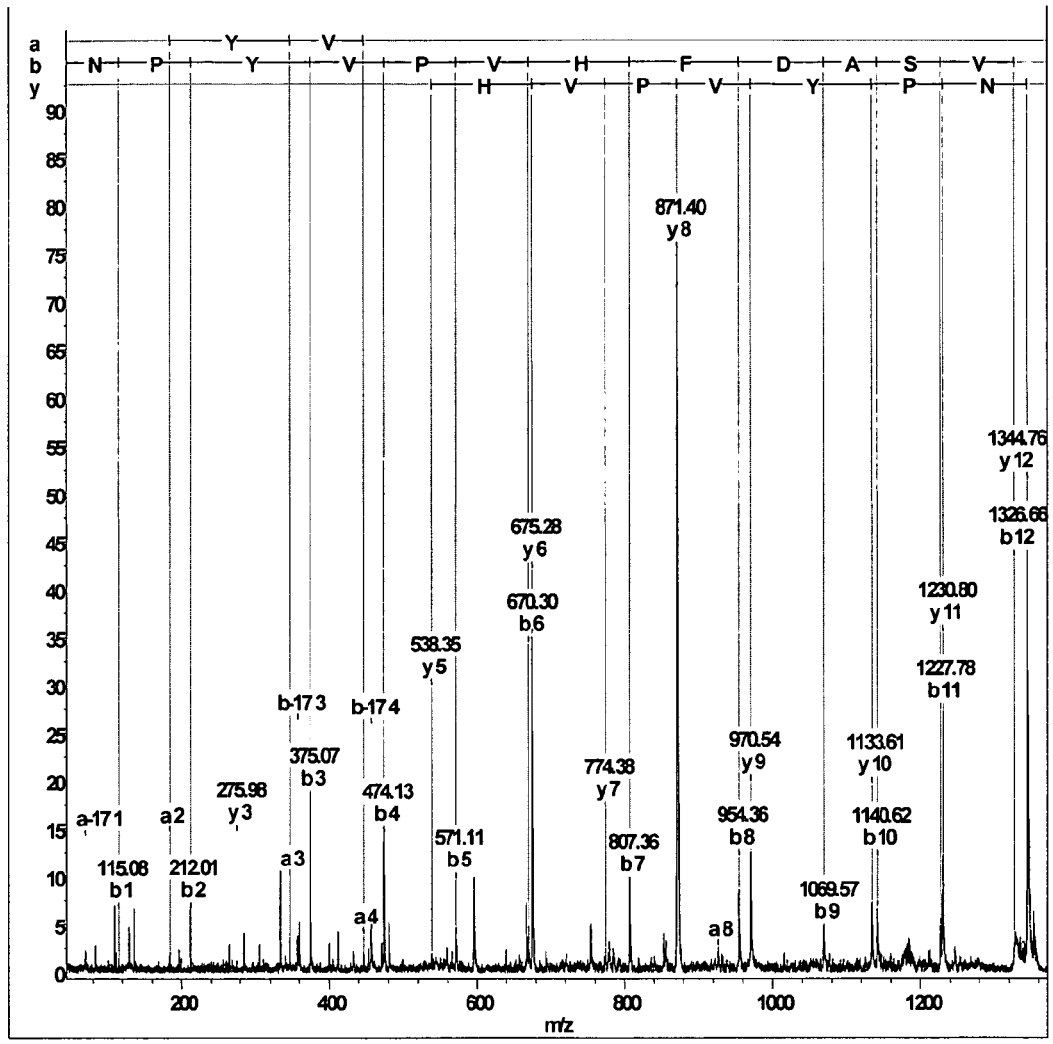

If the ISD fragment ions belong to the y series (FIG. 5 shows an ISD-LID granddaughter ion spectrum of a $y_{12}$ ISD fragment ion) then the metastable decay creates ISD-LID granddaughter ions of the b and the y series, again with a low admixture of other series and again up to the C-terminus in each case. Here too, the indexing of the b ions is related to the ISD fragment ion, not to the original protein. The correct sequence pattern of the RNase-B at the C-terminus is confirmed here, as well.

The invention is therefore eminently suitable for checking the terminal sequence of a known protein, for example for quality control. At this point, attention should be drawn to the fact that there is practically no other method for confirming the sequence at the C-terminus. The Edman sequencing fails here, as do other mass spectrometric methods.—The invention can, however, also be used for a so-called de-novo determination of terminal protein sequences.

Figure 6:
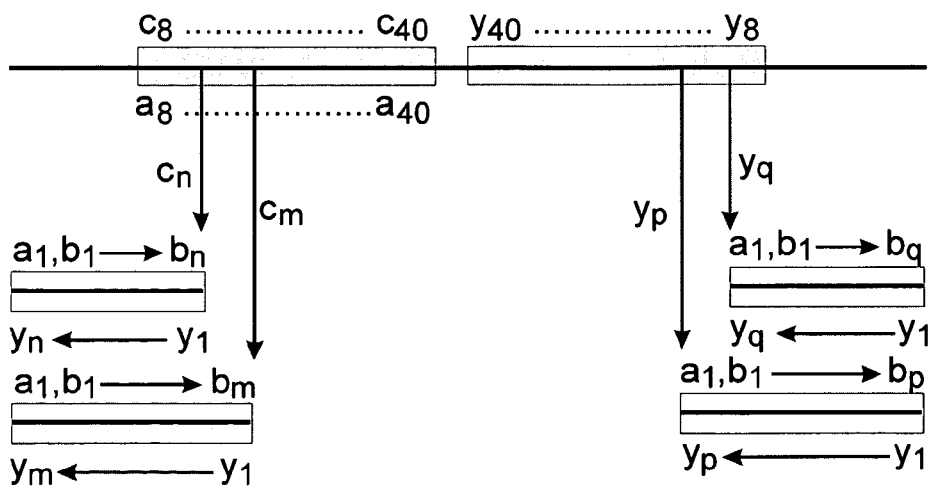
FIG. 6 depicts a favorable schematic of a spectrum acquisition for the simple de-novo sequencing of terminal sequences.

For the de-novo determination of N-terminal sequences, it is expedient to obtain two (or more) granddaughter ion spectra from several c ISD fragment ions. These c fragment ions can usually be identified in the ISD fragment ion spectrum as prominent ion signals (see FIG. 2) or they can be identified using ISD spectra with CHCA or sinapic acid as the matrix. In the different granddaughter ion spectra (preferably recorded with DHB as matrix) the b and y fragmentation ion series in the different granddaughter ion spectra shift in opposite directions, as schematically represented in FIG. 6. From a comparison of the granddaughter ion spectra, therefore, the b and y ion series of the N-terminal peptide amide ions can be identified by their shift and extracted; in this way, practically pure b and y series of the granddaughter ions can be read out. This reading out of pure b and y ion series can be automated by use of a computer program, for example.

The N-terminal sequence of the proteins can now be simply read off from the mass differences of the extracted b ion series of the terminal protein amide ions in the c type granddaughter ion spectrum. As is always the case with the determination of the protein sequences from the differences between mass signals, it is not possible to discriminate between the two amino acid building blocks leucine and isoleucine because they have the same mass. The two amino acids lysine and glutamine, which differ only by 36 milli mass units, can only be discriminated by very accurate mass determinations. All other amino acids differ by at least one atomic mass unit. This problem is common to all mass spectrometric sequence determinations and is accordingly taken into consideration in all commercial bioinformatic computer programs. Hence, when the sequence determination of proteins or peptides is mentioned here, the discrimination between leucine and isoleucine, and usually the discrimination between lysine and glutamine as well, is always left open.

Analog to this, the C-terminal sequence can be obtained from two (or more) granddaughter ion spectra from y ISD fragment ions. The y ISD fragment ions remain in the ISD spectra recorded with DHB as matrix as residue, if the a and c ions are left out of the consideration as identified. It should be made clear again at this point that the identification of the C-terminal sequence with this invention is practically unique and hence of inestimable value.

If the y or b series break off in the ISD fragment ion spectrum, this means there is a cross link. In this case, the cross link can be dissolved using biochemical means. The disulfide bridges between cysteines can be dissolved by an oxidation, for example, and also by a reduction followed by an alkylation.

For complete sequence determinations of smaller proteins and larger peptides, both N-terminal and C-terminal ISD fragment ions can be selected with such a size that, in the middle of the molecule, a large overlapping of the sequence can be seen, making it possible to put the terminal sequences on both sides together to form a total sequence. Each of the ISD fragment ions selected for the granddaughter ion spectra must therefore be heavier than half the total molecule (more precisely: the sum of the masses of two examined fragment ions must be around at least four amino acids bigger than the total mass of the molecule examined).

For the most complete sequence determination of very large proteins, it is favorable to digest the proteins with an enzyme, to separate the digest peptides from each other by selective methods (chromatography or electrophoresis) and to then feed them separately into the analysis using the method according to the invention. In this case it is advisable not to choose a tryptic digest, which supplies split segments with an average length of only 10 amino acids because of its splitting at two different types of amino acids, but to choose an enzyme that only splits at one type of amino acid and hence generates split segments with an average length of 20 amino acids.

As already described above, the invention is especially useful for checking a presumed sequence, for example for quality controls of synthetic proteins. The syntheses can be of a chemical nature, or of a recombinant nature, e.g. in bacteria. Particularly in the case of recombinant synthesis of the proteins it is difficult to produce a clean sequence of the protein chain ends.

For automatic quality control of the synthesis of proteins, ISD-LID granddaughter ion spectra from a large number of ISD fragment ions of a preselected mass range, for example from 1000 to 2000 atomic mass units, can be automatically measured with a TOF/TOF mass spectrometer. By using a suitable computer program to automatically annotate with the presumed correct terminal sequence, confirmations of this sequence can automatically be found. If spectra are found for which annotations with the correct sequence make no sense, or which demonstrate a mass shift at the terminal, then the protein is not correctly synthesized. A comparison of different granddaughter ion spectra allows terminal b or y series of granddaughter ions to be found which indicate the type of modification during the synthesis.

The described acquisition, according to the invention, of granddaughter ion spectra which contain information about terminal sequences of proteins can also be obtained using other types of second fragmentation of the ISD fragment ions. TOF/TOF mass spectrometers often include the possibility of collision fragmentation (CID), which according to the invention can be used in addition to metastable decay (LID). Collision fragmentation also provides w and d ions which can be used to discriminate between leucine and isoleucine.

Other types of tandem mass spectrometers can also be used for the acquisition of spectra according to the method of the invention, however, for example, the combination of quadrupole filter mass spectrometer and time-of-flight mass spectrometer with orthogonal ion injection, when they are equipped with an ion source for ionization by means of matrix-assisted laser desorption. It must, however, be borne in mind that no ions below the mass threshold can be stored in the collision cell and in the ion guides, which are usually designed as quadrupole, hexapole or octapole rod systems, and that these light ions are therefore lost. All high frequency multipole rod systems have a lower mass limit for the ion storage capability.

High frequency quadrupole ion trap mass spectrometers are not particularly favorable for this invention because they also have a lower mass limit for the storage of the ions. In contrast, Fourier transform mass spectrometers are very good when they are equipped with MALDI ion sources. In these types of spectrometers, which have no lower mass limit, the ISD fragment ions can be broken down into granddaughter ions by means of collision fragmentation (CID) and also infrared multiphoton dissociation (IRMPD).

The less frequently used fragmentation of ions on suitably prepared surfaces (SID=surface induced decomposition) can also be used. Tandem mass spectrometers with this type of fragmentation are known.

What is claimed is:

1. Method for the acquisition of a mass spectrum containing information about sequences of a biopolymer, in a tandem mass spectrometer with an ion source for the ionization of the biopolymer by means of matrix-assisted laser desorption, the method comprising:
   (a) preparing the biopolymer together with a matrix substance as a sample on a sample support;
   (b) placing the sample support in the ion source;
   (c) bombarding the sample on the sample support with light pulses from a pulsed laser with such a high energy density that it causes spontaneous fragmentations of a part of the biopolymer molecules whereby different species of in-source decay ISD fragment ions are formed;
   (d) accelerating the ions and injecting them into a first mass spectrometer of the tandem mass spectrometer;
   (e) selecting one species of the ISD fragment ions in the first mass spectrometer of the tandem mass spectrometer;
   (f) fragmenting the selected ISD fragment ions at least partially to granddaughter ions by means of gas collisions (CID), surface collisions (SID) photon collisions (PID) or metastable decay (LID); and
   (g) measuring the granddaughter ions in a second mass spectrometer of the tandem mass spectrometer to form a granddaughter mass spectrum.

2. Method according to claim 1 wherein the tandem mass spectrometer is a tandem in time mass spectrometer.

3. Method according to claim 1 wherein the tandem mass spectrometer is a tandem in space mass spectrometer.

4. Method according to claim 3, wherein the tandem in space mass spectrometer comprises one of the grourp consisting of magnetic sector mass spectrometers, quadrupole filter mass spectrometers, ion trap mass spectrometers and time-of-flight mass spectrometers.

5. Method according to claim 1, wherein the tandem mass spectrometer comprises a quadrupole filter as the first mass spectrometer and a time-of-flight mass spectrometer with orthogonal ion injection as the second mass spectrometer.

6. Method according to claim 1, wherein the tandem mass spectrometer comprises two coaxially aligned time-of-flight mass spectrometers (TOF/TOF).

7. Method according to claim 1, wherein the formation of the granddaughter mass spectrum is preceded by an acquisition of a mass spectrum of ISD fragment ions generated in the ion source by the laser bombardment and wherein the mass spectrum of the ISD fragment ions serves as a base for the selection of the one species of ISD fragment ions for the formation of the granddaughter mass spectrum.

8. Method according to claim 7, wherein the biopolymers are proteins and wherein more than one mass spectrum of the ISD fragment ions is acquired prior to the formation of the granddaughter mass spectrum, and for each one of the mass spectra of the ISD fragment ions, a different matrix substance is used to form ISD fragment ions.

9. Method according to claim 7, wherein the biopolymers are proteins and prior to the formation of the granddaughter mass spectrum, cross links of the proteins are dissolved.

10. Method according to claim 9, wherein disulfide bridges between cysteines are dissolved by reduction and alkylation, or by oxidation.

11. Method according to claim 1, wherein the tandem mass spectrometer is an ion trap mass spectrometer and wherein the selection, fragmentation and measuring of the granddaughter ions are carried out in the ion trap mass spectrometer consecutively.

12. Method for the determination of terminal sequences of a protein using a tandem mass spectrometer, the method comprising:
(a) acquiring granddaughter mass spectra of different species of in-source decay ISD fragment ion of the same fragmentation series, each granddaughter mass spectrum being acquired by
  (i) preparing the protein together with a matrix substance as a sample on a sample support;
  (ii) placing the sample support in the ion source;
  (iii) bombarding the sample on the sample support with light pulses from a pulsed laser with such a high energy density that it causes spontaneous fragmentations of a part of the protein whereby different species of ISD fragment ions are formed;
  (iv) accelerating the ions and injecting them into a first mass spectrometer of the tandem mass spectrometer;
  (v) selecting one species of the ISD fragment ions in the first mass spectrometer of the tandem mass spectrometer;
  (vi) fragmenting the selected ISD fragment ions at least partially to granddaughter ions by means of gas collisions (CID), surface collisions (SID) photon collisions (PID) or metastable decay (LID); and
  (vii) measuring the granddaughter ions in a second mass spectrometer of the tandem mass spectrometer to form a granddaughter mass spectrum;
(b) comparing the granddaughter mass spectra to determine one fixed ion fragmentation series that is not shifted on all of the granddaughter mass spectra; and
(c) using the mass differences of the fixed ion fragmentation series to read out the terminal sequence of the protein.

13. Method according to claim 12, wherein a computer program is used to identify the fixed ion fragmentation series in the granddaughter mass spectra.

14. Method according to claim 13, wherein the determination read out of the terminal sequence is also performed by means of a computer program.

* * * * *